(12) United States Patent
Avinash et al.

(10) Patent No.: US 7,397,886 B2
(45) Date of Patent: Jul. 8, 2008

(54) METHOD AND APPARATUS FOR SOFT-TISSUE VOLUME VISUALIZATION

(75) Inventors: Gopal B. Avinash, New Berlin, WI (US); John Michael Sabol, Sussex, WI (US); Matthew Joseph Walker, New Berlin, WI (US)

(73) Assignee: General Electric Company, Schenectady, NY (US)

( * ) Notice: Subject to any disclaimer, the term of this patent is extended or adjusted under 35 U.S.C. 154(b) by 60 days.

(21) Appl. No.: 11/101,888

(22) Filed: Apr. 7, 2005

(65) Prior Publication Data

US 2005/0180541 A1 Aug. 18, 2005

Related U.S. Application Data

(63) Continuation of application No. 10/306,468, filed on Nov. 27, 2002, now Pat. No. 6,898,263.

(51) Int. Cl.
*G21K 1/12* (2006.01)
(52) U.S. Cl. .................. 378/5; 378/4; 378/901
(58) Field of Classification Search ........... 378/4, 378/5, 9, 19, 98.9, 901, 98.8, 65
See application file for complete search history.

(56) References Cited

U.S. PATENT DOCUMENTS

| | | | |
|---|---|---|---|
| 5,782,762 A | 7/1998 | Vining | |
| 5,812,691 A | 9/1998 | Udupa et al. | |
| 5,813,984 A | 9/1998 | Haaga et al. | |
| 5,838,758 A * | 11/1998 | Krug et al. | 378/53 |
| 5,953,444 A | 9/1999 | Joseph et al. | |
| 6,016,439 A | 1/2000 | Acker | |
| 6,069,634 A | 5/2000 | Gibson | |
| 6,083,162 A | 7/2000 | Vining | |
| 6,106,464 A | 8/2000 | Bass et al. | |
| 6,169,817 B1 | 1/2001 | Parker et al. | |
| 6,246,747 B1 | 6/2001 | Wear et al. | |
| 6,272,366 B1 | 8/2001 | Vining | |
| 6,317,621 B1 | 11/2001 | Graumann et al. | |
| 6,556,196 B1 | 4/2003 | Blanz et al. | |
| 6,574,302 B2 | 6/2003 | Adriaansz | |
| 6,585,647 B1 | 7/2003 | Winder | |
| 6,694,163 B1 | 2/2004 | Vining | |
| 6,728,331 B1 * | 4/2004 | McDaniel et al. | 378/4 |
| 6,898,263 B2 * | 5/2005 | Avinash et al. | 378/4 |
| 6,917,697 B2 * | 7/2005 | Avinash et al. | 382/132 |
| 2003/0197704 A1 * | 10/2003 | Tek et al. | 345/474 |
| 2004/0028181 A1 * | 2/2004 | Charles, Jr. et al. | 378/92 |

\* cited by examiner

*Primary Examiner*—Irakli Kiknadze
*Assistant Examiner*—Christine Moore
(74) *Attorney, Agent, or Firm*—Armstrong Teasdale LLP

(57) ABSTRACT

A method for obtaining data including scanning an object using a multi-energy computed tomography (MECT) system to obtain data to generate an anatomical image, and decomposing the obtained data to generate a first density image representative of bone material and a second density image representative of soft-tissue. The method further includes segmenting at least one of the first density image and the second density image, and volume rendering the second density image.

20 Claims, 8 Drawing Sheets

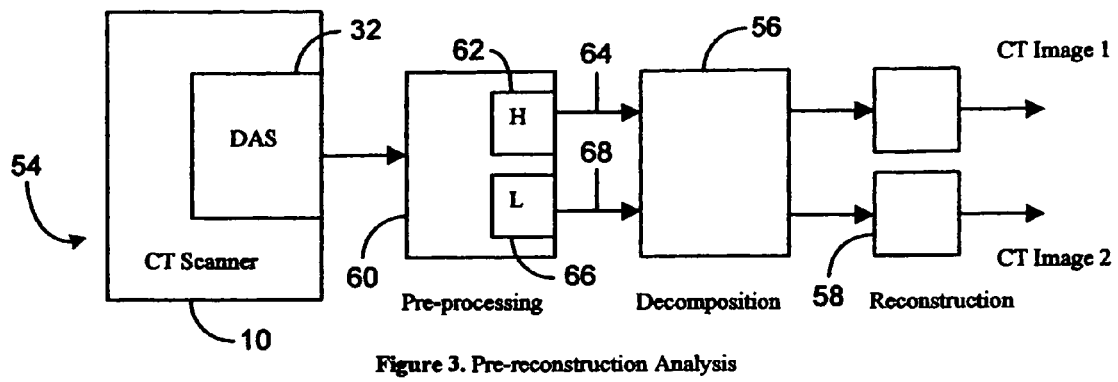
Figure 3. Pre-reconstruction Analysis
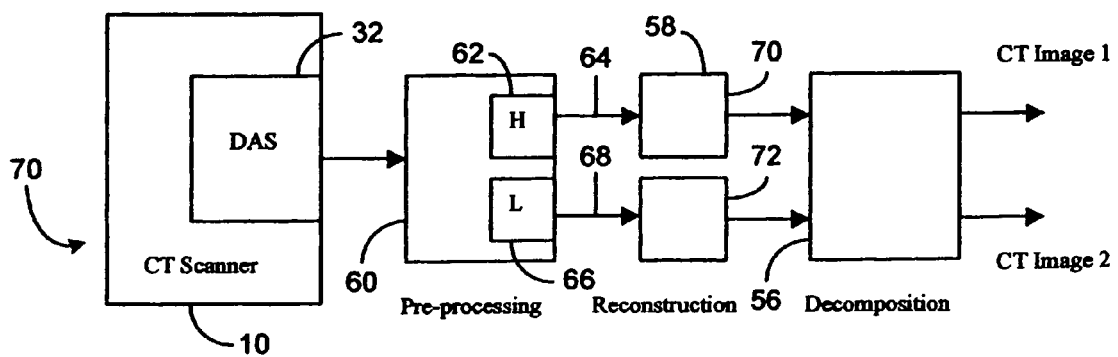
Figure 4. Post-reconstruction Analysis

METHOD AND APPARATUS FOR SOFT-TISSUE VOLUME VISUALIZATION

CROSS REFERENCE TO RELATED APPLICATIONS

This application is a continuation of U.S. patent application Ser. No. 10/306,468, filed Nov. 27, 2002 now U.S. Pat. No. 6,898,263, which is hereby incorporated by reference in its entirety.

BACKGROUND OF THE INVENTION

This invention relates generally to medical imaging systems, and more specifically to a method and apparatus for soft-tissue volume visualization using a medical imaging system.

In spite of recent advancements in computed tomography (CT) technology, such as faster scanning speed, larger coverage with multiple detector rows, and thinner slices, energy resolution is still a missing piece, namely, a wide x-ray photon energy spectrum from the x-ray source and a lack of energy resolution from CT detection systems preclude energy discrimination CT.

X-ray attenuation through a given object is not a constant. Rather, x-ray attenuation is strongly dependent on the x-ray photon energy. This physical phenomenon manifests itself in an image as a beam-hardening artifact, such as non-uniformity, shading, and streaks. Some beam-hardening artifacts can be easily corrected, but others may be more difficult to correct. In general, known methods to correct beam hardening artifacts include water calibration, which includes calibrating each CT machine to remove beam hardening from materials similar to water, and iterative bone correction, wherein bones are separated in the first-pass image then correcting for beam hardening from bones in the second-pass. However, beam hardening from materials other than water and bone, such as metals and contrast agents, may be difficult to correct. In addition, even with the above described correction methods, conventional CT does not provide quantitative image values. Rather, the same material at different locations often shows different CT numbers.

Another drawback of conventional CT is a lack of material characterization. For example, a highly attenuating material with a low density can result in the same CT number in the image as a less attenuating material with a high density. Thus, there is little or no information about the material composition of a scanned object based solely on the CT number.

Additionally, similar to traditional x-ray methods, at least some known soft-tissue volume visualization methods project rays through an object. However, without segmenting out bone from other material within the object, visualization of subtle, yet possibly diagnostically important, structures may be difficult. Traditionally, bone segmentation of CT images is based on image characteristics and Hounsfield numbers. Dual-energy decomposition lends itself nicely for the soft-tissue and bone separation. However, the methods and systems described below can also remove calcification, which contains diagnostic information in CT.

BRIEF DESCRIPTION OF THE INVENTION

In one aspect, a method for obtaining data is provided. The method includes scanning an object using a multi-energy computed tomography (MECT) system to obtain data to generate an anatomical image, and decomposing the obtained data to generate a first density image representative of bone material and a second density image representative of soft-tissue. The method further includes segmenting at least one of the first density image and the second density image, and volume rendering the second density image.

In another aspect, a multi-energy computed tomography (MECT) system is provided. The MECT includes at least one radiation source, at least one radiation detector, and a computer operationally coupled to the radiation source and the radiation detector. The computer is configured to receive data regarding a first energy spectrum of a scan of an object, receive data regarding a second energy spectrum of the scan of the object, decompose the received data to generate a first density image representative of bone material and a second density image representative of soft-tissue, identify within the first density image areas smaller than a predetermined size, and import data into the second density image from the data regarding the first energy spectrum according to the identified areas of the first density image.

In a further aspect, a multi-energy computed tomography (MECT) system is provided. The CT system includes at least one radiation source, at least one radiation detector, and a computer operationally coupled to the radiation source and the radiation detector. The computer is configured to receive image data for an object, decompose the received image data into a first density image representative of bone material and a second density image representative of soft-tissue, identify within the first density image areas smaller than a predetermined size, and extract the identified areas within the first density image using an algorithm configured to use the connectivity of binary pixels.

In an additional aspect, a computer readable medium embedded with a program is provided. The computer readable medium is configured to instruct a computer to receive data regarding a first energy spectrum of a scan of an object, receive data regarding a second energy spectrum of the scan of the object, decompose the received data to generate a first density image representative of bone material and a second density image representative of soft-tissue, threshold the first density image to produce a first binary mask image representing bone and calcification, extract areas identified as smaller than a predetermined size from the first binary mask image to produce a second binary mask image substantially representing calcification, and import data into the second density image from the received data according to the extracted areas of the first binary mask image.

In yet another aspect, a method is provided for obtaining data. The method includes scanning an object using a multi-energy computed tomography (MECT) system to obtain data to generate an anatomical image, decomposing the obtained data to generate a first density image and a second density image, and volume rendering at least one of the first and second density image.

BRIEF DESCRIPTION OF THE DRAWINGS

FIG. 3 is a flow chart representing a pre-reconstruction analysis.

FIG. 4 is a flow chart representing a post-reconstruction analysis.

DETAILED DESCRIPTION OF THE INVENTION

Figure 1:
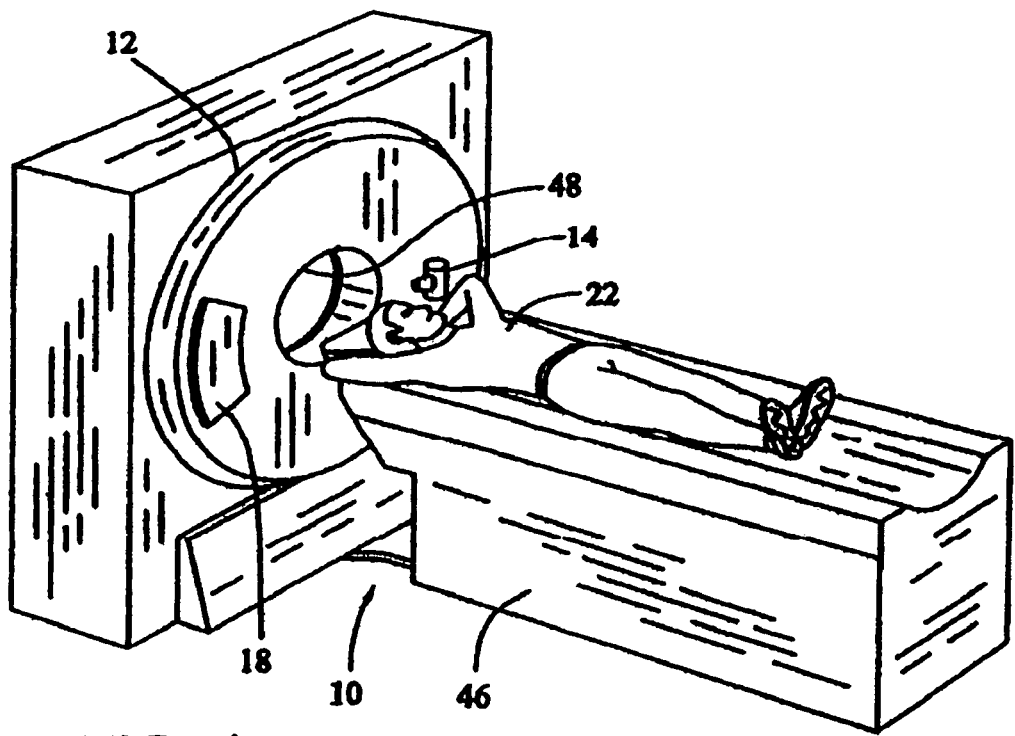
FIG. 1 is a pictorial view of a MECT imaging system.

The methods and apparatus described herein facilitate augmenting segmentation capabilities of multi-energy imaging with a method for image-based segmentation. The methods and systems described herein facilitate real-time volume buildup and visualization of soft-tissue. More specifically, the methods and systems described herein facilitate segmenting bone material from an image while retaining calcification within the image, and facilitate augmenting segmentation capabilities of multi-energy imaging to guide surgical navigation and radiation therapy.

In some known CT imaging system configurations, an x-ray source projects a fan-shaped beam which is collimated to lie within an x-y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as the filtered backprojection technique. This process converts the attenuation measurements from a scan into integers called "CT numbers" or "Hounsfield units" (HU), which are used to control the brightness of a corresponding pixel on a cathode ray tube display.

To reduce the total scan time, a "helical" scan may be performed, wherein the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The weighted data is then processed to generate CT numbers and to construct an image that corresponds to a two-dimensional slice taken through the object.

To further reduce the total acquisition time, multi-slice CT has been introduced. In multi-slice CT, multiple rows of projection data are acquired simultaneously at any time instant. When combined with helical scan mode, the system generates a single helix of cone beam projection data Similar to the single slice helical, weighting scheme, a method can be derived to multiply the weight with the projection data prior to the filtered backprojection algorithm.

As used herein, an element or step recited in the singular and proceeded with the word "a" or "an" should be understood as not excluding plural said elements or steps, unless such exclusion is explicitly recited. Furthermore, references to "one embodiment" of the methods and systems described herein are not intended to be interpreted as excluding the existence of additional embodiments that also incorporate the recited features.

Also as used herein, the phrase "reconstructing an image" is not intended to exclude embodiments of the methods and systems described herein in which data representing an image is generated but a viewable image is not. However, many embodiments generate (or are configured to generate) at least one viewable image.

Herein are described methods and apparatus for tissue characterization and soft-tissue volume visualization using an energy-discriminating (also known as multi-energy) computed tomography (MECT) system. First described is MECT system 10 and followed by applications using MECT system 10.

Figure 2:
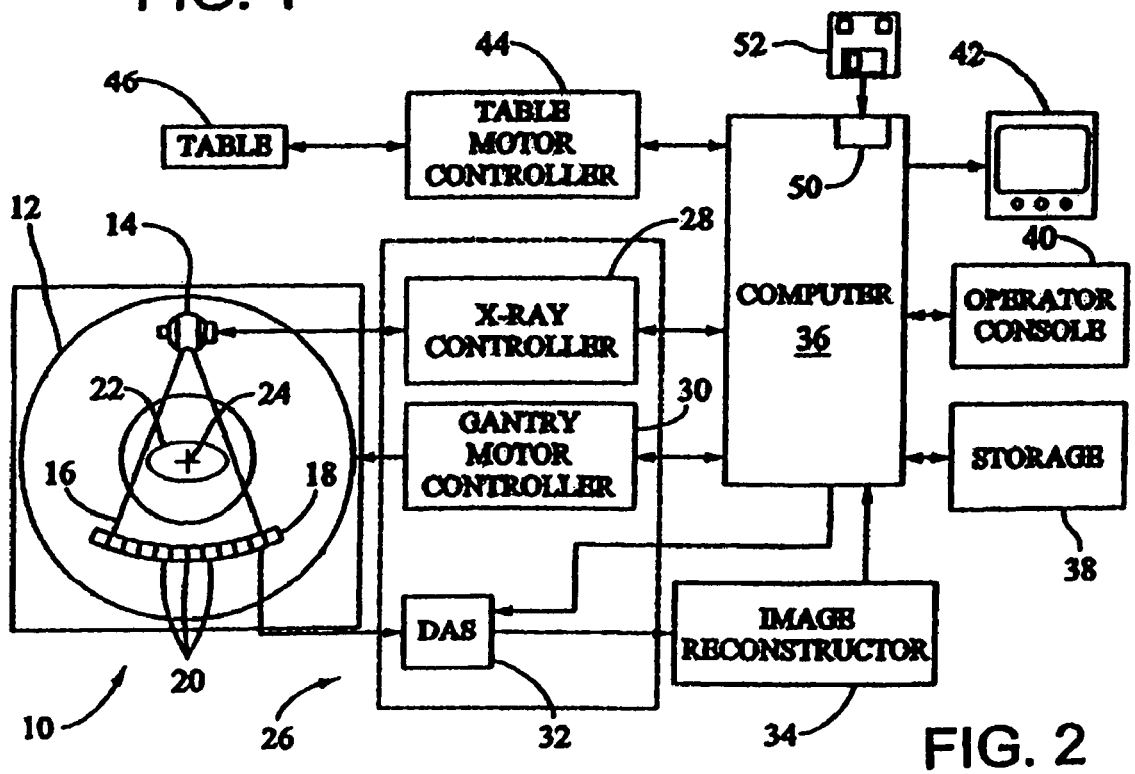
FIG. 2 is a block schematic diagram of the system illustrated in FIG. 1.

Referring to FIGS. 1 and 2, a multi-energy scanning imaging system, for example, a multi-energy multi-slice computed tomography (MECT) imaging system 10, is shown as including a gantry 12 representative of a "third generation" CT imaging system. Gantry 12 has an x-ray source 14 that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22. Each detector element 20 produces an electrical signal that represents the intensity of an impinging x-ray beam and hence can be used to estimate the attenuation of the beam as it passes through object or patient 22. During a scan to acquire x-ray projection data, gantry 12 and the components mounted therein rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan.

Rotation of components on gantry 12 and the operation of x-ray source 14 are governed by a control mechanism 26 of MECT system 10. Control mechanism 26 includes an x-ray controller 28 that provides power and timing signals to x-ray source 14 and a gantry motor controller 30 that controls the rotational speed and position of components on gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36, which stores the image in a storage device 38.

Image reconstructor 34 can be specialized hardware or computer programs executing on computer 36.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or an other digital source such as a network or the Internet, as well as yet to be developed digital devices. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. CT imaging system 10 is an energy-discriminating (also known as multi-energy) computed tomography (MECT) system in that system 10 is configured to be responsive to different x-ray spectra. This can be accomplished with a conventional third generation CT system to acquire projections sequentially at different x-ray tube potentials. For example, two scans are acquired either back to back or interleaved in which the tube operates at 80 kVp and 160 kVp potentials, for example. Alternatively, special filters are placed between the x-ray source and the detector such that different detector rows collect projections of different x-ray energy spectrum. Alternatively, the special filters that shape the x-ray spectrum can be used for two scans that are acquired either back to back or interleaved. Yet another embodiment is to use energy sensitive detectors such that each x-ray photon reaching the detector is recorded with its photon energy. Although the specific embodiment mentioned above refers to a third generation CT system, the methods described herein equally apply to fourth generation CT systems (stationary detector—rotating x-ray source) and fifth generation CT systems (stationary detector and x-ray source).

There are different methods to obtain multi-energy measurements: (1) scan with two distinctive energy spectra, (2) detect photon energy according to energy deposition in the detector, and (3) photon counting. Photon counting provides clean spectra separation and an adjustable energy separation point for balancing photon statistics.

MECT facilitates reducing or eliminating a plurality of problems associated with conventional CT, such as, but not limited to, a lack of energy discrimination and material characterization. In the absence of object scatter, one only need system 10 to separately detect two regions of photon energy spectrum, the low-energy and the high-energy portions of the incident x-ray spectrum. The behavior at any other energy can be derived based on the signal from the two energy regions. This phenomenon is driven by the fundamental fact that in the energy region where medical CT is interested, two physical processes dominate the x-ray attenuation, (1) Compton scatter and the (2) photoelectric effect. Thus, detected signals from two energy regions provide sufficient information to resolve the energy dependence of the material being imaged. Furthermore, detected signals from two energy regions provide sufficient information to determine the relative composition of an object composed of two materials.

In an exemplary embodiment, MECT decomposes a high-energy image and a low-energy image using a decomposition method, such as through a CT number difference decomposition, a Compton and photoelectric decomposition, a basis material decomposition (BMD), or a logarithm subtraction decomposition (LSD).

The CT number difference algorithm includes calculating a difference value in a CT or a Hounsfield number between two images obtained at different tube potentials. In one embodiment, the difference values are calculated on a pixel-by-pixel basis. In another embodiment, average CT number differences are calculated over a region of interest. The Compton and photoelectric decomposition includes acquiring a pair of images using MECT 10, and separately representing the attenuations from Compton and photoelectric processes. The BMD includes acquiring two CT images, wherein each image represents the equivalent density of one of the basis materials. Since a material density is independent of x-ray photon energy, these images are approximately free of beam-hardening artifacts. Additionally, an operator can choose the basis material to target a certain material of interest, thus enhancing the image contrast. In use, the BMD algorithm is based on the concept that the x-ray attenuation (in the energy region for medical CT) of any given material can be represented by proper density mix of other two given materials, accordingly, these two materials are called the basis materials. In one embodiment, using the LSD, the images are acquired with quasi-monoenergetic x-ray spectra, and the imaged object can be characterized by an effective attenuation coefficient for each of the two materials, therefore the LSD does not incorporate beam-hardening corrections. Additionally, the LSD is not calibrated, but uses a determination of the tissue cancellation parameters, which are the ratio of the effective attenuation coefficient of a given material at the average energy of each exposure. In an exemplary embodiment, the tissue cancellation parameter is primarily dependent upon the spectra used to acquire the images, and on any additional factors that change the measured signal intensity from that which would be expected for a pair of ideal, mono-energetic exposures.

It should be noted that in order to optimize a multi-energy CT system, the larger the spectra separation, the better the image quality. Also, the photon statistics in these two energy regions should be similar, otherwise, the poorer statistical region will dominate the image noise.

The methods and systems described herein apply the above principle to tissue characterization and soft-tissue volume visualization. In specific, ME CT system 10 is utilized to produce CT images as herein described. Pre-reconstruction analysis, post-reconstruction analysis and scout image analysis are three techniques that can be used with MECT system 10 to provide tissue characterization.

FIG. 3 is a flow chart representing a pre-reconstruction analysis 54 wherein a decomposition 56 is accomplished prior to a reconstruction 58. Computer 36 collects the acquired projection data generated by detector array 18 (shown in FIG. 1) at discrete angular positions of the rotating gantry 12 (shown in FIG. 1), and passes the signals to a preprocessor 60. Preprocessor 60 re-sorts the projection data received from computer 36 to optimize the sequence for the subsequent mathematical processing. Preprocessor 60 also corrects the projection data from computer 36 for detector temperature, intensity of the primary beam, gain and offset, and other deterministic error factors. Preprocessor 60 then extracts data corresponding to a high-energy view 62 and routes it to a high-energy channel path 64, and routes the data corresponding to a low-energy views 66 to a low-energy path 68. Using the high-energy data and low-energy data, a decomposition algorithm is used to produce two streams of projection data, which are then reconstructed to obtain two individual images pertaining to two different materials.

FIG. 4 is a flow chart representing a post-reconstruction analysis wherein decomposition 56 is accomplished after reconstruction 58. Computer 36 collects the acquired projection data generated by detector array 18 (shown in FIG. 1) at discrete angular positions of rotating gantry 12 (shown in FIG. 1), and routes the data corresponding to high-energy views 62 to high-energy path 64 and routes the data corresponding to low-energy views 66 to low-energy path 68. A first CT image 70 corresponding to the high-energy series of projections 62 and a second CT image 72 corresponding to low-energy series of projections 66 are reconstructed 58. Decomposition 56 is then performed to obtain two individual images respectively, pertaining to two different materials. In scout image analysis, the signal flow can be similar to FIG. 3 or FIG. 4. However, the table is moved relative to the non-rotating gantry to acquire the data.

The use of dual energy techniques in projection x-ray imaging may facilitate diagnosing and monitoring osteoporosis, and determining an average fat-tissue to lean-tissue ratio (fat/lean ratio). Dual energy techniques may also facilitate cross-sectional or tomographic x-ray imaging for osteoporosis detection in human subjects, and may facilitate non-destructive testing applications, for example explosive and/or contraband detection.

The methods and systems described herein apply multi-energy imaging to volume visualization. Techniques that allow visualization of three-dimensional data are referred to as volume rendering. More specifically, volume rendering is a technique used for visualizing sampled functions of three: spatial dimensions by computing 2-D projections of a semi-transparent volume. Volume rendering is applied to medical imaging, wherein volume data is available from X-ray CT scanners. CT scanners produce three-dimensional stacks of parallel plane images, or slices, each of which consist of an array of X-ray absorption coefficients. Typical X-ray CT images have a resolution of 512×512×12 bits, and include up to 500 slices in a stack. In the two-dimensional domain, slices can be viewed one at a time. An advantage of CT images over conventional X-ray images is that each slice only contains information from one plane. A conventional X-ray image, on the other hand, contains information from all planes, and the result is an accumulation of shadows that are a function of the density of anything that absorbs X-rays, for example tissue, bone, organs, etc. The availability of the stacks of parallel data produced by CT scanners prompted the development of techniques for viewing the data as a three-dimensional field, rather than as individual slices. Therefore, the CT image data can now be viewed from any viewpoint.

A number of different methods are used for viewing CT image data as a three-dimensional field, for example, including rendering voxels in a binary partitioned space, marching cubes, and ray casting. When rendering voxels in a binary partitioned space, choices are made for the entire voxel. This may produce a "blocky" image. In addition, rendering voxels in a binary partitioned space may result in a lack of dynamic range in the computed surface normals, which will produce images with relatively poor shading.

Using marching cubes for viewing CT image data in a three-dimensional field solves some of the problems associated with rendering voxels in a binary partitioned space. However, using marching cubes requires that a binary decision be made as to the position of the intermediate surface that is extracted and rendered. Furthermore, extracting an intermediate structure may cause false positives (artifacts that do not exist) and false negatives (discarding small or poorly defined features).

Using ray casting for viewing CT image data in a three-dimensional field facilitates use of the three-dimensional data without attempting to impose any geometric structure on it. Ray casting solves one of the most important limitations of surface extraction techniques, namely the way in which surface extraction techniques display a projection of a thin shell in the acquisition space. More specifically, surface extraction techniques fail to take into account that, particularly in medical imaging, data may originate from fluid and other materials, which may be partially transparent and should be modeled as such. Ray casting, however, does take into account that data may originate from fluid and other materials, and can model materials that are partially transparent.

Figure 5:
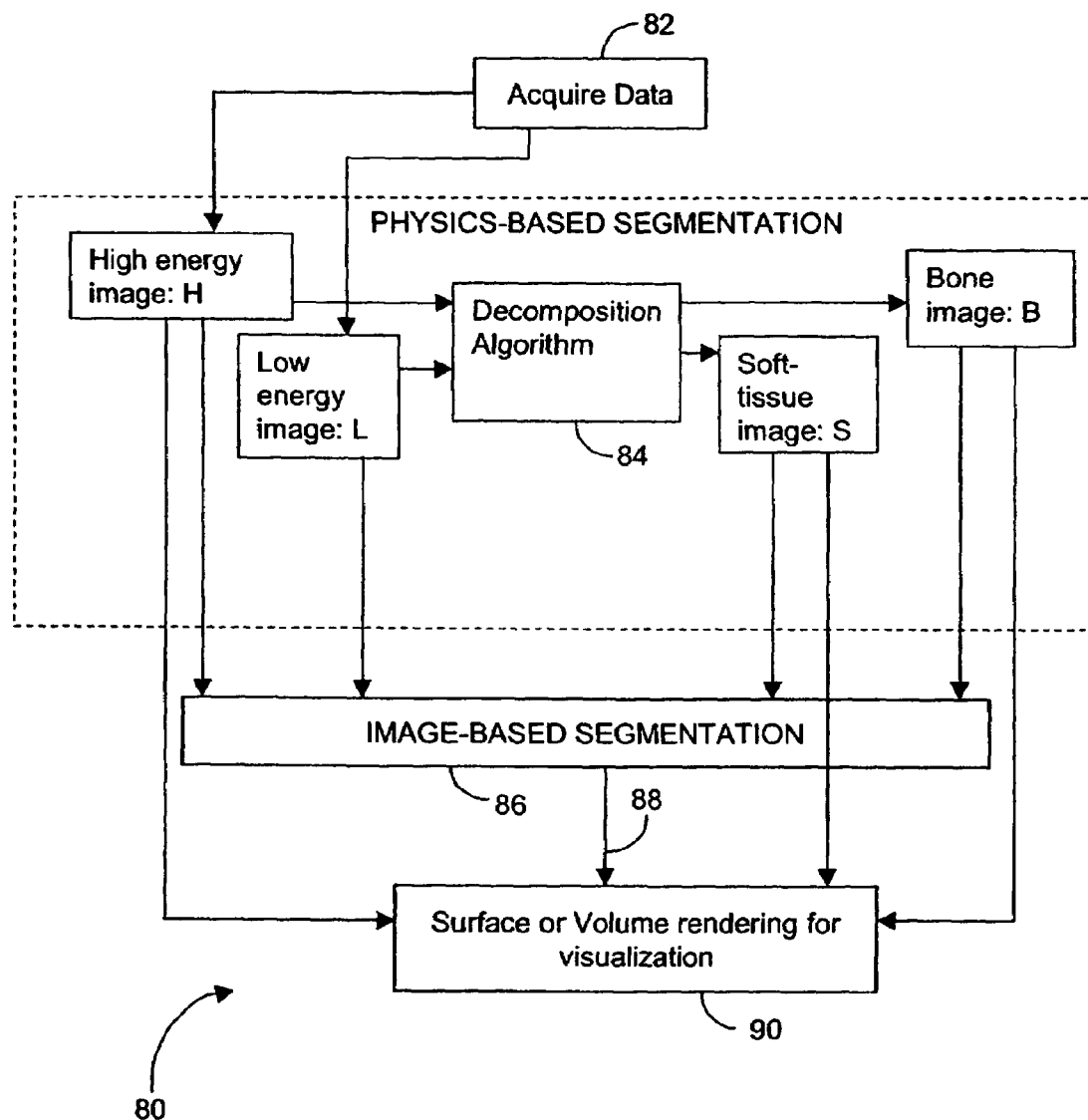
FIG. 5 is a schematic illustration of a method for volume visualization using the MECT imaging system illustrated in FIGS. 1 and 2.

FIG. 5 is a schematic illustration of a method 80 for soft-tissue volume visualization using MECT system 10 (shown in FIGS. 1 and 2). Method 80 describes 3D visualization using a combination of physics-based segmentation (multi-energy decomposition data) and image-based segmentation. More specifically, method 80 includes acquiring 82 MECT anatomic image data for an object (not shown), wherein the anatomic image data includes a high-energy image (H) and a low-energy image (L). The anatomic image data is then decomposed 84 to obtain a density image representing soft-tissue within the object and a density image representing bone material within the object. The high-energy image, low-energy image, soft-tissue density image, and bone-material density image are then segmented 86 using image-based segmentation to determine a region of interest within the object. In one embodiment, high-energy image, low-energy image, the soft-tissue density image, and the bone-material density image are segmented 86 individually using image-based segmentation. In another embodiment, high-energy image, low-energy image, the soft-tissue density image, and the bone-material density image are segmented 86 in combination using image-based segmentation.

Several segmentation techniques can be used for image-based segmentation to determine a region of interest within the object, including, but not limited to, Hounsfield or CT number (threshold) techniques, iterative thresholding, k-means segmentation, edge detection, edge linking, curve fitting, curve smoothing, 2D/3D morphological filtering, region growing, fuzzy clustering, image/volume measurements, heuristics, knowledge-based rules, decision trees, and neural networks. Segmentation of a region of interest can be performed manually and/or automatically. In one embodiment, the high-energy image, the low-energy image, the soft-tissue density image, and the bone-material density image are segmented manually to determine a region of interest within the object by displaying the data and a user delineating the region of interest using a mouse or any other suitable interface, for example, a touch screen, eye-tracking, and/or voice commands. In addition, in one embodiment, the high-energy image, the low-energy image, the soft-tissue density image, and the bone-material density image are automatically segmented to determine a region of interest with the object by using an algorithm that utilizes prior knowledge, such as the shape and size of a mass, to automatically delineate the area of interest. In yet another embodiment, the high-energy image, the low-energy image, the soft-tissue density image, and the bone-material density image are segmented to determine a region of interest within the object semi-automatically by combining manual and automatic segmentation.

The image-based segmented high-energy anatomical image data, the image-based segmented soft-tissue density image, and the image-based segmented bone density image are then used 88 to obtain a soft-tissue image including bone material for the region of interest within the object. The soft-tissue image including bone material is then used to build a three-dimensional image, which in turn is used for rendering 90 to provide high-contrast rendered images. In an alternative embodiment, the high-energy image, the low-energy image, the soft-tissue density image, and the bone-material density image are not segmented 86, but rather, at least one of the high-energy image, the low-energy image, the soft-tissue density image, and the bone-material density image are used to build a three-dimensional image, which is used for rendering 90 to provide high-contrast rendered images. Rendering 90 is performed using conventional rendering techniques, such as, for example, techniques describe in *The Visualization Toolkit, An Object-Orientated Approach to 3D Graphics*, Will Shroeder, Ken Martin, and Bill Lorensen, Prentice-Hall 1996. In one embodiment, volume rendering is used to provide high-contrast rendered images. In another embodiment, surface rendering is used to provide high-contrast rendered images.

Figure 6:
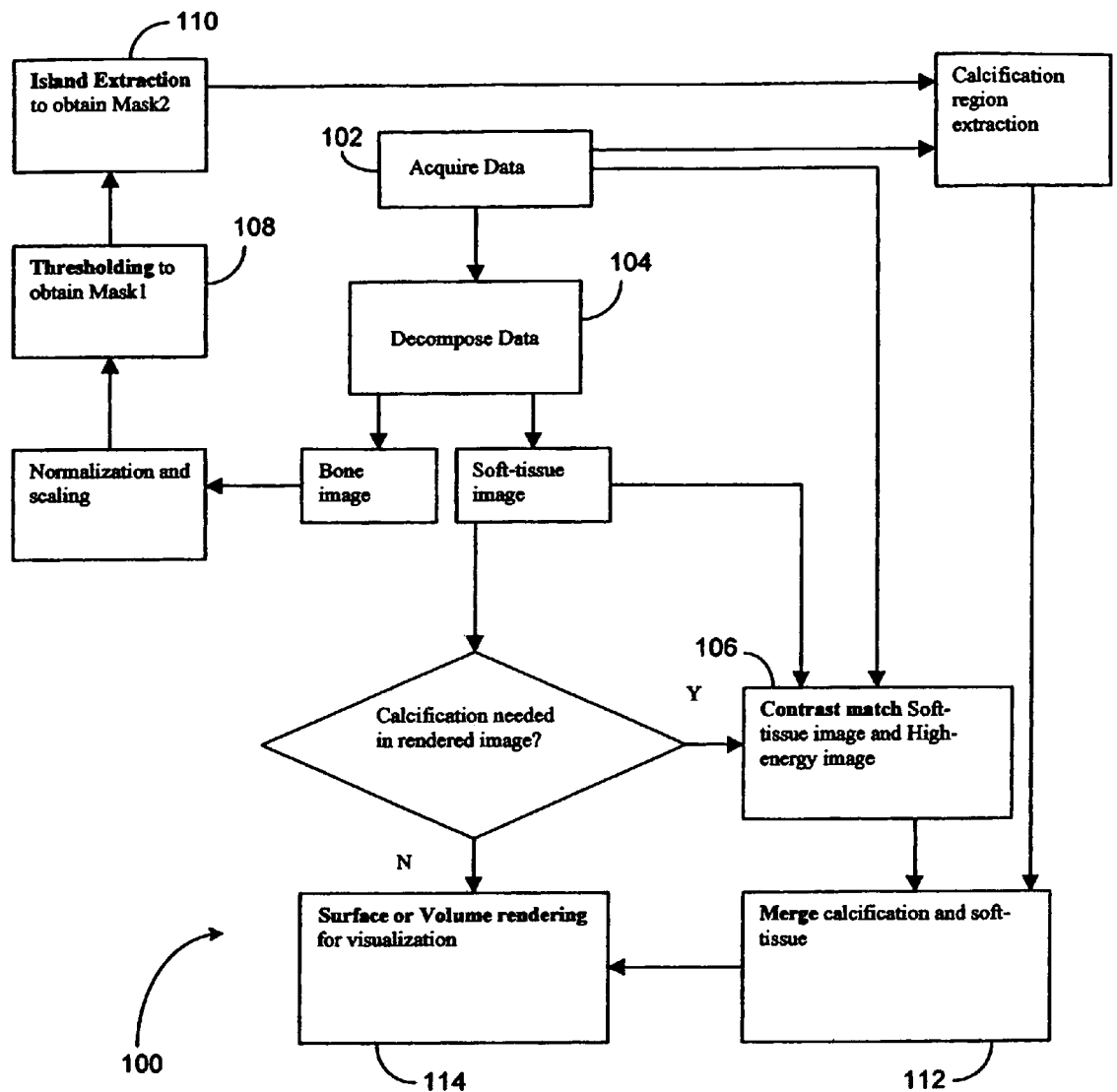
FIG. 6 is a schematic illustration of a method for soft-tissue volume visualization using the MECT imaging system illustrated in FIGS. 1 and 2.

FIG. 6 is a schematic illustration of a method 100 for soft-tissue volume visualization using MECT system 10 (shown in FIGS. 1 and 2). More specifically, method 100 is a specific example of one embodiment of method 80. In use, method 100 includes acquiring 102 MECT anatomic image data for a region of interest within an object (not shown) or, alternatively, the object in its entirety, wherein the anatomic image data includes a high-energy image and a low-energy image. The anatomic image data is then decomposed 104 to obtain a density image representing soft-tissue within the region of interest ($I_s$) and a density image representing bone-material within the region of interest ($I_b$). In one embodiment, the density image representing soft-tissue is obtained using the following decomposition equation:

$$I_s = \frac{H}{L^{w_s}},$$

where $0 < w_s < w_b < 1$. Additionally, and in one embodiment, the density image representing bone-material is obtained using the following decomposition equation:

$$I_b = \frac{H}{L^{w_b}},$$

where $0 < w_s < w_b < 1$.

The density image representing soft-tissue is then contrast matched 106 with a standard CT image of the region of interest. For example, in the exemplary embodiment, the contrast of structures within the soft-tissue density image are matched with the corresponding structures in the high-energy anatomical image data H. In one embodiment, the soft-tissue density image is contrast matched 106 with the high-energy anatomical image data H by solving the above decomposition equations for H in terms of $I_s$, $I_b$, $w_b$, and $w_s$, to obtain the following relationship:

$$H = I_s^{\frac{w_b}{w_b - w_s}} I_b^{\frac{-w_s}{w_b - w_s}}.$$

By differentiation of the logarithm of the above equation, the following contrast equation is derived:

$$C(H) = \frac{w_b}{w_b - w_s} C(I_s) - \frac{w_s}{w_b - w_s} C(I_b),$$

wherein C(.) represents the contrast in the image. From the above C(H) equation, it may be evident that while matching the contrast in the soft-tissue density image and the corresponding structures in the high-energy anatomical image data, the contrast [C($I_b$)] resulting from the bone-material density image may need to be suppressed. In one embodiment, to reduce the fine-detail contrast while preserving the scaling, the bone-material density image is low-pass filtered such that all structural information is eliminated. Accordingly, a contrast matched soft-tissue image ($I_{HS}$) is obtained from the following equation:

$$I_{HS} = I_s^{\frac{w_b}{w_b - w_s}} LPF\left(I_b^{\frac{-w_s}{w_b - w_s}}\right),$$

wherein the function LPF(.) performs the low-pass filtering of the bone-material density image. In one embodiment, a boxcar filter is used as LPF(.) to perform low-pass filtering of the image, wherein the boxcar filter smoothes an image by the average of a given neighborhood. Using boxcar filtering, each point in an image requires only four arithmetic operations, irrespective of kernel size. In addition, and in one embodiment, the length of the separable kernel is variable. In an alternative embodiment, a bone mask is derived by segmenting the bone image. The bone mask is inverted to obtain the soft-tissue mask. The inverted bone mask is superimposed on the soft-tissue image and the soft-tissue regions are contrast-matched to the soft-tissue regions of the standard image. Special care is taken at the borders of the mask to alleviate problems resulting from the bone-soft-tissue transition region. In one embodiment, the border regions can be rank-order filtered, for example, using median criterion to suppress high intensity transition rings in 3D. The resulting image is a contrast-matched soft-tissue image.

The bone-material density image is then thresholded 108 to produce a first binary mask image containing bone and calcification. More specifically, because the bone-material density image includes both calcium and bone, the bone-material density image is thresholded 108 to separate out high-contrast bone regions and the high-contrast calcification regions from the low-contrast regions. Islands smaller than a pre-specified size are then extracted 110 from the first binary mask image to produce a second binary mask image corresponding substantially to calcification. In one embodiment, an algorithm using the connectivity of binary pixels is used to extract 110 small islands from the first binary mask image to produce the second binary mask image. For example, in one embodiment four-connectivity is used to determine the size of connected components and extract 110 islands smaller than the prespecified limit to produce the second binary mask image. In another embodiment, eight-connectivity is used to determine the size of connected components and extract 110 islands smaller than the pre-specified limit to produce the second binary mask image.

The original pixel values from the high-energy anatomical image data that correspond to the second binary mask image are then merged 112 with the contrast-matched soft-tissue image to obtain a soft-tissue image including calcification. More specifically, the regions within the high-energy anatomical image data that correspond to the second binary mask image are extracted from the high-energy anatomical image and merged with the contrast-matched soft-tissue image to produce a soft-tissue image including calcification. The soft-tissue image including calcification is then used to build a three-dimensional image, which in turn is used for rendering 114 to provide high-contrast rendered images. Rendering 114 is performed using conventional rendering techniques, such as, for example, techniques describe in *The Visualization Toolkit, An Object-Orientated Approach to 3D Graphics*, Will Shroeder, Ken Martin, and Bill Lorensen, Prentice-Hall 1996. In one embodiment, volume rendering is used to provide high-contrast rendered images. In another embodiment, surface rendering is used to provide high-contrast rendered images. In an alternative embodiment wherein calcification identification is not desired for visualization, normalized soft-tissue image data is used to produce three-dimensional renderings of soft-tissue.

Figure 7:
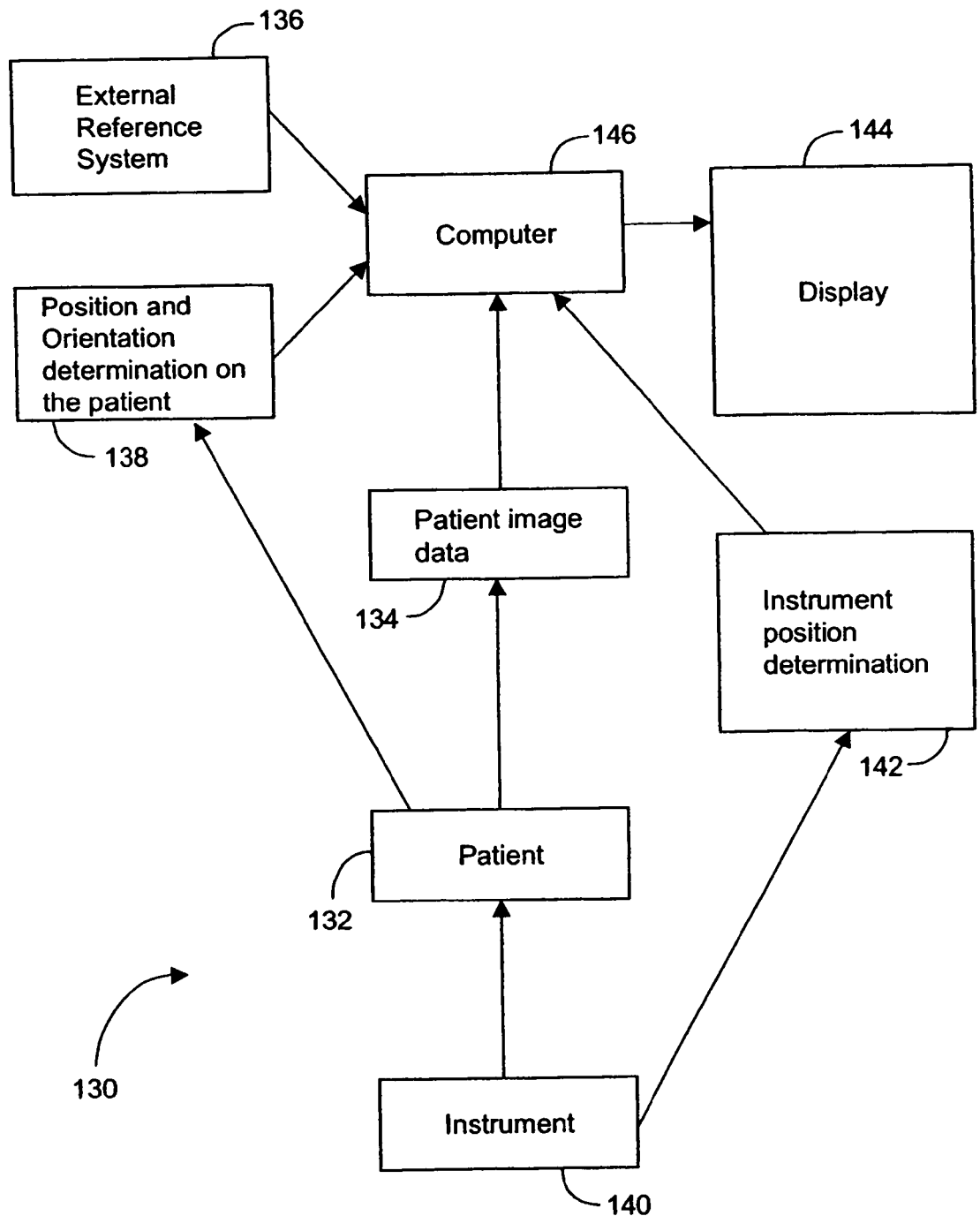
FIG. 7 is a schematic illustration of a known surgical navigation system.

FIG. 7 is a schematic illustration of a known surgical navigation system 130. System 130 includes a surgical patient 132, image data 134 for patient 132, a reference means 136 having a reference point on a reference coordinate system that is external to patient 132, a position and orientation determination means 138 coupled to patient 132 for determining the position and orientation of patient 132, a surgical instrument 140, a surgical instrument position determination means 142 coupled to instrument 140 for determining the position of surgical instrument 140, and a display 144 coupled to a computer 146. Computer 146 converts patient display data to objective display data, converts instrument location and orientation data for display on display 144, and provides a known relationship between patient 132 and the reference point. Computer 146 displays patient image data 134 and instrument 140 on display 144 substantially simultaneously.

Figure 8:
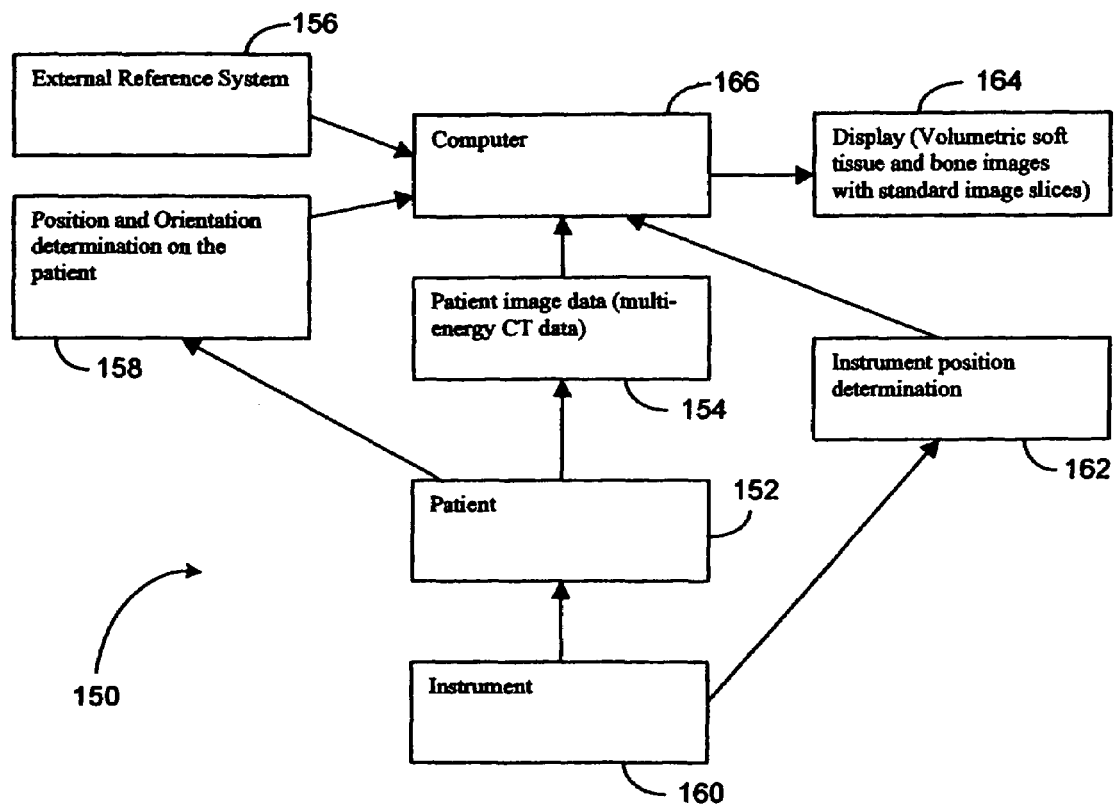
FIG. 8 is a schematic illustration of a surgical navigation system for use with the method described in FIG. 5.

FIG. 8 is a schematic illustration of a surgical navigation system 150 for use with method 80 (shown in FIG. 5) to provide surgical instrument mapping for two volumes simultaneously and assist in identification of subtle soft-tissue structures and their spatial relationship to bone. System 150 includes a surgical patient 152, image data 154 for patient 152 including multi-energy CT data, a reference means 156 having a reference point on a reference coordinate system that is external to patient 152, a position and orientation determination means 158 coupled to patient 152 for determining the position and orientation of patient 152, a surgical instrument 160, a surgical instrument position determination means 162 coupled to instrument 160 for determining the position of surgical instrument 160, and a display 164 coupled to a computer 166. Computer 166 converts patient display data to objective display data, converts instrument location and orientation data for display on display 164, and provides a known relationship between patient 152 and the reference point. Computer 166 displays patient image data 154 and instrument 160 on display 164 substantially simultaneously. In addition, computer 166 displays a standard image of patient image data 154 on display 164, displays a soft-tissue only image of patient image data 154 on display 164, and displays a bone-only image of patient image data 154 on display 164. In one embodiment, computer 166 displays the standard image, the soft-tissue only image, and the bone-only image substantially simultaneously. In another embodiment, computer 166 includes a toggling capability for toggling between display of the standard image, the soft-tissue only image, and the bone-only image on display 164.

Figure 9:
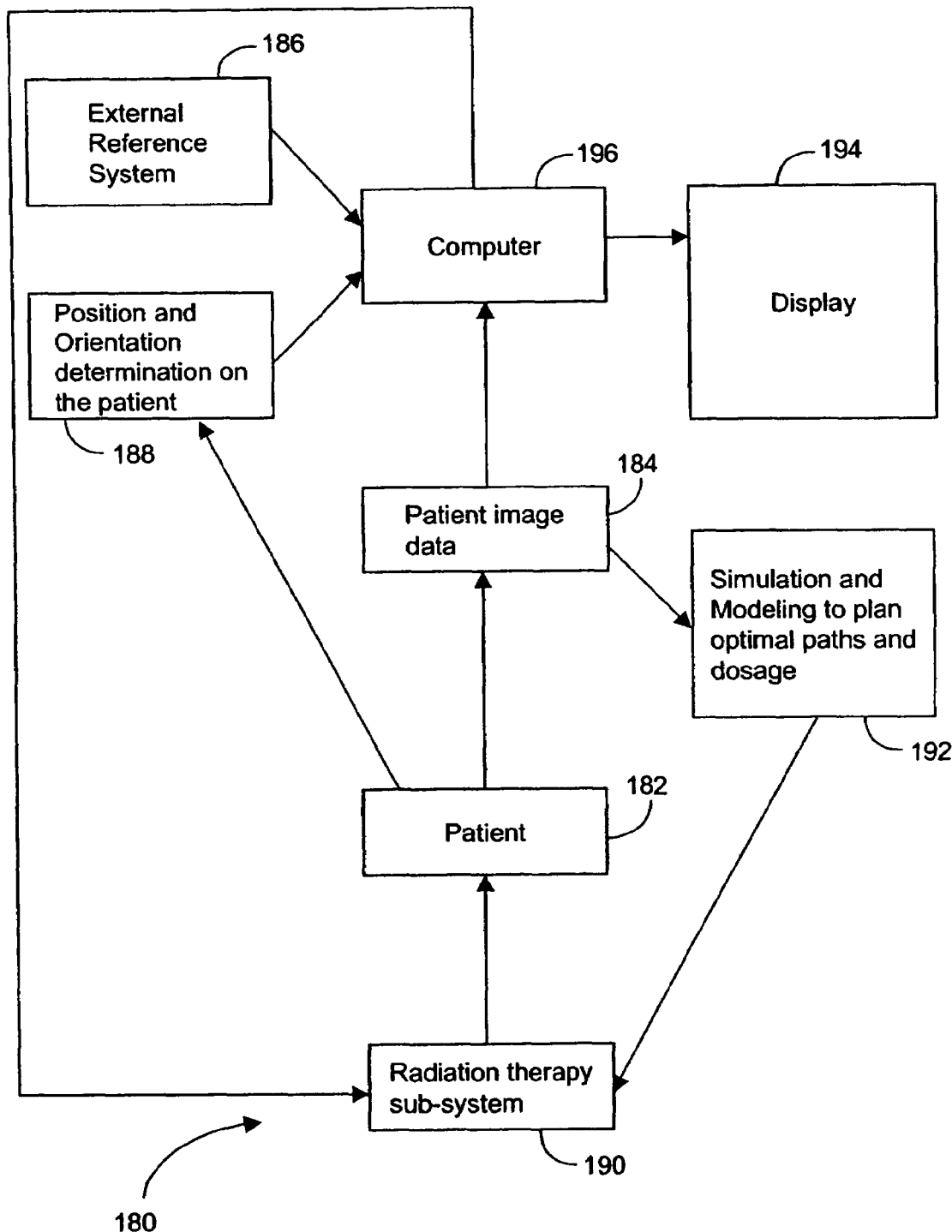
FIG. 9 is a schematic illustration of a known radiation therapy system.

FIG. 9 is a schematic illustration of a known radiation system 180. System 180 includes a radiation therapy patient 182, image data 184 for patient 182, a reference means 186 having a reference point on a reference coordinate system that is external to patient 182, a position and orientation determination means 188 coupled to patient 182 for determining the position and orientation of patient 182, a radiation therapy sub-system 190, a simulation and modeling means 192 for planning paths and dosage, and a display 194 coupled to a computer 196. Computer 146 converts patient display data to objective display data, converts radiation localization for display on display 194, and provides a known relationship between patient 182 and the reference point. Computer 196 displays patient image data 184 and the radiation localization on display 194 substantially simultaneously.

Figure 10:
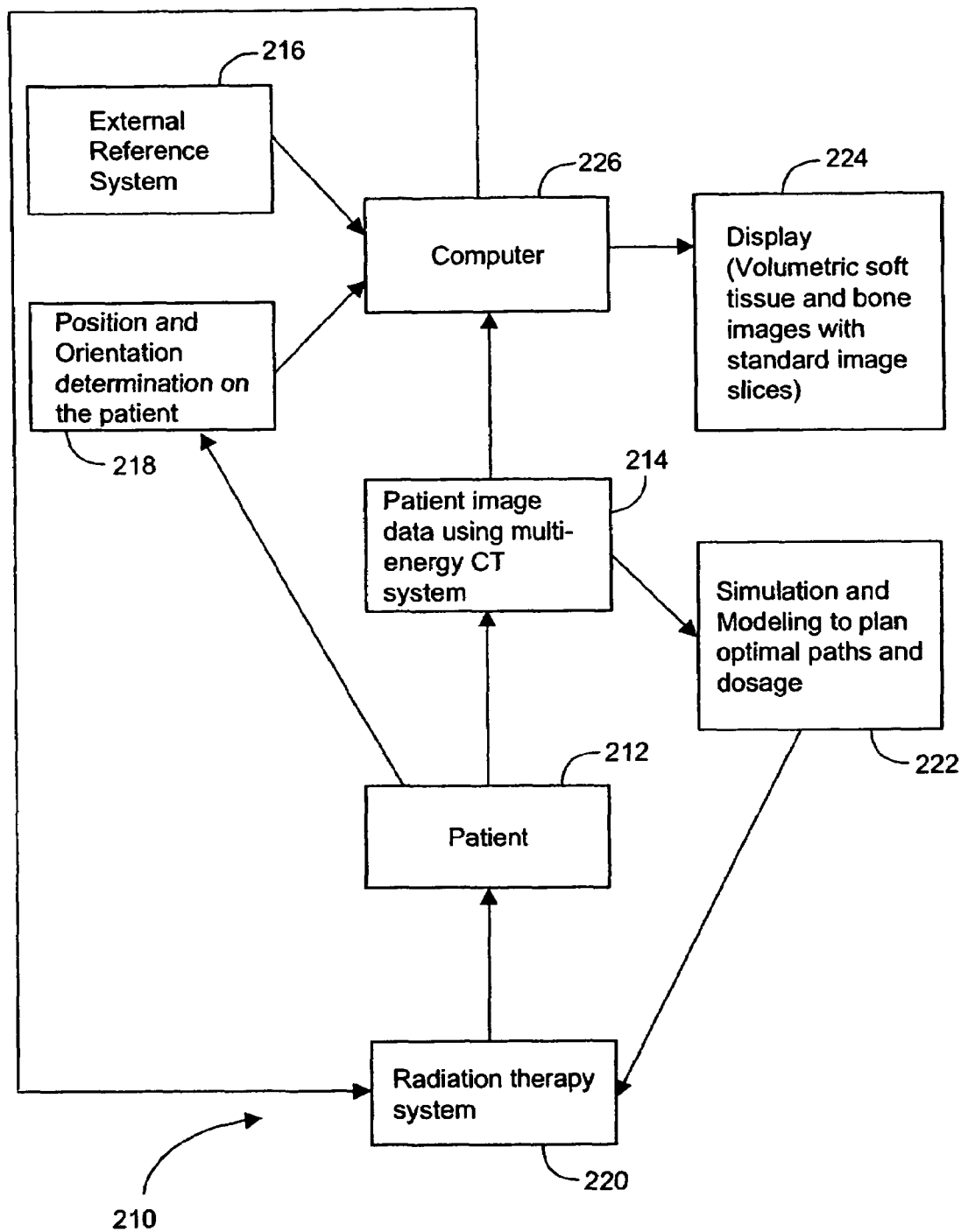
FIG. 10 is a schematic illustration of a radiation therapy system for use with the method described in FIG. 5.

FIG. 10 is a schematic illustration of a radiation system 210 for use with method 80 (shown in FIG. 5) to provide radiation therapy planning and simulation calculations. System 210 includes a radiation therapy patient 212, image data 214 for patient 212 including multi-energy CT image data, a reference means 216 having a reference point on a reference coordinate system that is external to patient 212, a position and orientation determination means 218 coupled to patient 212 for determining the position and orientation of patient 212, a radiation therapy sub-system 220, a simulation and modeling means 222 for planning paths and dosage, and a display 224 coupled to a computer 226. Computer 226 converts patient display data to objective display data, converts radiation localization for display on display 224, and provides a known relationship between patient 212 and the reference point. Computer 226 displays patient image data 184 and the radiation localization on display 194 substantially simultaneously. In addition, computer 226 displays a standard image of patient image data 214 on display 224, displays a soft-tissue only image of patient image data 214 on display 224, and displays a bone-only image of patient image data 214 on display 224. In one embodiment, computer 226 displays the standard image, the soft-tissue only image, and the bone-only image substantially simultaneously. In another embodiment, computer 226 includes a toggling capability for toggling between display of the standard image, the soft-tissue only image, and the bone-only image on display 224.

The above-described methods and systems facilitate augmenting segmentation capabilities of multi-energy imaging with a method for image-based segmentation, and may facilitate real-time volume buildup and visualization of soft-tissue. More specifically, the above-described methods and systems facilitate segmenting bone material from an image while retaining calcification within the image, facilitate providing traditional surgical instrument mapping for two volumes simultaneously, facilitate identification of subtle soft-tissue structures and their spatial relationship to bone, facilitate computer simulation of dosage and paths for radiation therapy, and facilitate improving radiation therapy planning and simulation calculations.

Exemplary embodiments of MECT methods and systems are described above in detail. The methods and systems are not limited to the specific embodiments described herein, but rather, components of each method and system may be utilized independently and separately from other components described herein. In addition, each method and system component can also be used in combination with other components described herein.

While the invention has been described in terms of various specific embodiments, those skilled in the art will recognize that the invention can be practiced with modification within the spirit and scope of the claims.

What is claimed is:

1. A method for obtaining data, said method comprising:
accessing multi-energy computed tomography (MECT) scanned image data for an object;
decomposing the accessed data into a first density image representative of bone material and a second density image representative of soft-tissue;
identifying, within the first density image, areas smaller than a predetermined size;
extracting the identified areas within the first density image using an algorithm configured to use the connectivity of binary pixels; and
displaying the obtained image data, the first density image, and the second density image on a display to facilitate radiation therapy planning and simulation calculations.

2. A method in accordance with claim 1 further comprising thresholding the first density image to produce a first binary mask image representing bone and calcification; and
extracting the identified areas with the first density image from the first binary mask image to produce a second binary mask image substantially representing calcification.

3. A method in accordance with claim 2 further comprising importing data into the second density image from the accessed image data according to the identified areas in the first density image.

4. A method in accordance with claim 1 further comprising contrast matching the second density image with the received image data to produce a contrast-matched soft-tissue image.

5. A method in accordance with claim 4 further comprising importing data into the contrast-matched soft-tissue image from the received imaged data according to the identified areas of the first density image;
building a three-dimensional image using the contrast matched soft-tissue image including the imported data; and
rendering the three-dimensional image using at least one of volume and surface rendering to produce a high-contrast rendered image.

6. A multi-energy computed tomography (MECT) system for inspection of objects, said system comprising:
at least one radiation source;
at least one radiation detector; and
a computer operationally coupled to said radiation source and said radiation detector, said computer configured to:
receive scanned image data of an object scanned by said system;
decompose said received image data into a first density image representative of a first material and a second density image representative of a second material;
segment at least one of the first density image and the second density image; and
volume render the second density image.

7. A system in accordance with claim 6 wherein said volume rendered density image is further configured to identify image areas smaller than a predetermined size, extract said identified areas within the said first density image using an algorithm configured to use connectivity of binary pixels, threshold said first density image to produce a first binary mask image, and extract said identified areas within said first density image from said first binary mask image to produce a second binary mask image.

8. A system in accordance with claim 7 wherein said computer configured to import data into said second density image from said received image data according to said identified areas in said first density image.

9. A system in accordance with claim 6 wherein said computer further configured to contrast match said second density image with said received image data to produce a contrast-matched soft-tissue image.

10. A system in accordance with claim 9 wherein said computer further configured to:
import data into said contrast-matched soft-tissue image from said received image data according to said identified areas of said first density image;
build a three-dimensional image using said contrast-matched soft-tissue image including said imported data; and
render said three-dimensional image using at least one of volume and surface rendering to produce a high-contrast rendered image.

11. A method for obtaining data, said method comprising:
accessing multi-energy computed tomography (MECT) scanned data of an object to generate a computed tomographic (CT) object image;
decomposing the accessed data to generate a first CT density image representative of a first material and a second CT density image representative of a second material;
segmenting at least one of the first CT density image and the second CT density image; and
volume rendering the second CT density image.

12. A method in accordance with claim 11 wherein said segmenting at least one of the first CT density image and the second CT density image comprises identifying, within the first density image, areas smaller than a predetermined size, and importing data into the second density image from the object image according to the identified areas of the first density image.

13. A method in accordance with claim 12 further comprising thresholding the first CT density image to produce a first binary mask image, and extracting areas identified as smaller than the predetermined size from the first binary mask image to produce a second binary mask image.

14. A computer readable medium embedded with a program configured to instruct a computer to:
receive data regarding a first energy spectrum of a scan of an object;
receive data regarding a second energy spectrum of the scan of the object;
decompose said received data to generate a first density image and a second density image;
threshold said first density image to produce a first binary mask image;
extract areas identified as smaller than a predetermined size from said first binary mask image to produce a second binary mask image; import data into said second density image from said received data according to said extracted areas of said first binary mask image; and
generate data representative of an image.

15. A computer readable medium in accordance with claim 14 wherein said program further configured to instruct said computer to contrast match said second density image with said received data regarding the first energy spectrum to produce a contrast-matched image.

16. A method for obtaining data, said method comprising:
scanning an object using a multi-energy computed tomography (MECT) system to obtain data to generate an image;
decomposing the obtained data to generate a first density image and a second density image; and
volume rendering at least one of the first and second density image.

17. A method in accordance with claim 16 further comprising at least one of storing at least one of the volume rendered first and second density images using a storage device and displaying at least one of the volume rendered first and second density images on a display.

18. A method in accordance with claim 16 further comprising thresholding said first density image to produce a first binary mask image.

19. A method in accordance with claim 18 wherein said scanning an object using an MECT system comprises scanning the object with a high-energy projection to obtain a high-energy image and scanning the object with a low-energy projection to obtain a low-energy image.

20. A method in accordance with claim 16 utilized for at least one of explosive detection or contraband detection.

* * * * *